(12) United States Patent
Redford

(10) Patent No.: US 9,139,803 B2
(45) Date of Patent: Sep. 22, 2015

(54) ETHANOL FERMENTATION METHODS AND SYSTEMS

(71) Applicant: POET RESEARCH, INC., Sioux Falls, SD (US)

(72) Inventor: Steven G Redford, Brandon, SD (US)

(73) Assignee: POET RESEARCH, INC, Sioux Falls, SD (US)

( * ) Notice: Subject to any disclaimer, the term of this patent is extended or adjusted under 35 U.S.C. 154(b) by 0 days.

(21) Appl. No.: 14/328,429

(22) Filed: Jul. 10, 2014

(65) Prior Publication Data

US 2015/0065758 A1    Mar. 5, 2015

Related U.S. Application Data

(60) Provisional application No. 61/844,898, filed on Jul. 11, 2013.

(51) Int. Cl.

| | |
|---|---|
| *C07C 29/86* | (2006.01) |
| *C12F 3/06* | (2006.01) |
| *B01D 11/02* | (2006.01) |
| *B01D 12/00* | (2006.01) |
| *C02F 3/00* | (2006.01) |
| *B01D 1/00* | (2006.01) |
| *B01J 19/24* | (2006.01) |
| *C07C 29/84* | (2006.01) |

(52) U.S. Cl.
CPC ... *C12F 3/06* (2013.01); *B01D 1/00* (2013.01); *B01D 11/0203* (2013.01); *B01D 12/00* (2013.01); *B01J 19/24* (2013.01); *C02F 3/00* (2013.01); *C07C 29/84* (2013.01); *B01J 2219/24* (2013.01)

(58) Field of Classification Search
CPC .................................................. C07C 29/86
USPC .......................................................... 568/918
See application file for complete search history.

(56) References Cited

U.S. PATENT DOCUMENTS

| | | | | |
|---|---|---|---|---|
| 7,122,709 | B2 * | 10/2006 | Fanselow et al. | 568/918 |
| 7,297,236 | B1 * | 11/2007 | Vander Griend | 202/153 |
| 8,449,728 | B2 | 5/2013 | Redford | |
| 2005/0239181 | A1 * | 10/2005 | Lewis et al. | 435/161 |
| 2015/0037857 | A1 | 2/2015 | Redford | |

* cited by examiner

*Primary Examiner* — Sikarl Witherspoon
(74) *Attorney, Agent, or Firm* — Edna Vassilovski

(57) ABSTRACT

Methods and systems for purifying feedstock-to-ethanol fermentation products are disclosed. The methods include the use of a solvent in the form of a supercritical fluid or liquid gas such as supercritical $CO_2$ or liquid $CO_2$ to dry fermentation beer solids, and/or to extract oil, ethanol, or ethanol and oil from fermentation beer or mixtures derived therefrom. Systems include a separations reactor having a first portion defined by walls that are impermeable to fermentation beer liquids joined to a second portion defined by walls that are impermeable to fermentation beer liquids by a third portion defined by walls that are permeable to fermentation beer liquids and impermeable to fermentation beer solids.

16 Claims, 3 Drawing Sheets

ETHANOL FERMENTATION METHODS AND SYSTEMS

CROSS-REFERENCE TO RELATED APPLICATIONS

This application claims priority to U.S. Provisional Application No. 61/844,898, having a filing date of Jul. 11, 2013. This provisional application is herein incorporated by reference in its entirety.

FIELD

This specification relates to ethanol production processes, for example cellulose-based feedstock-to-ethanol conversion processes, starch-based feedstock-to-ethanol conversion processes, such as corn-to-ethanol production processes, and systems implementing such processes. This specification also relates to methods of purifying fermentation products, processes, and methods for extracting ethanol produced in ethanol fermentation processes, as well as systems implementing such processes.

BACKGROUND

Ethanol can be produced from grain-based feedstocks, cellulosic feedstocks, and other plant material. In a conventional ethanol plant producing ethanol from corn, corn kernels are processed to separate the starch-containing material from other matter. The starch-containing material is then slurried with water and liquefied to facilitate saccharification and fermentation. The product of fermentation is beer, which comprises a liquid component including ethanol and water and a solids component including unfermented particulate matter.

According to a typical process used at conventional ethanol plants, the liquefaction of the starch-containing feedstock is done by 'cooking' the slurry at a temperature at or near the boiling point of water (e.g. in the range of 60-80 degrees C. or greater). According to an alternative process, developed and implemented by POET Research LLC, the assignee of the present application, and described for example in U.S. Patent Pub. No. 2005/0239181, raw starch may be converted and fermented without 'cooking' or liquefaction.

In a conventional ethanol plant, the fermentation beer product may undergo a distillation process to produce ethanol and stillage. The stillage, or wet solids, can be dried into distillers dried grains, an operation in which water is removed from the solids, typically in a gas-fired dryer.

SUMMARY

In some embodiments, the present disclosure relates to methods and systems for purifying fermentation products, for example as part of an overall feedstock-to-ethanol fermentation conversion process.

In some embodiments, the methods and systems for purifying fermentation products relates to the use of a novel solvent as regards ethanol fermentation processes to separate the liquids component of fermentation beer, which liquids component includes one or more of ethanol, oil, and water, from the solids component of fermentation beer.

In some embodiments, the methods and systems for purifying fermentation products relates to the use of the novel solvent to dry the solids component of fermentation beer. The drying methods and systems can be implemented before or after beer distillation.

In some embodiments, the methods and systems for purifying fermentation products relates to the use of the novel solvent to extract oil, extract oil and ethanol, and/or extract ethanol from other process components. The extraction methods and systems can be implemented anywhere during the process flow in which it may be desirable to separate ethanol from oil and/or other process components, or to separate ethanol and oil from other process components, or to separate oil from other process components.

In some embodiments, the methods for separating the liquids component of fermentation beer from the solids component of fermentation beer involve displacing the liquids portion from the solids portion with a solvent chosen from a supercritical fluid and liquid gas. In some embodiments, the solvent has a lighter density than ethanol, for example the solvent is supercritical $CO_2$ or liquid $CO_2$. In some embodiments, displacing involves contacting the fermentation beer with the solvent in an extractor resulting in a solids stream including solvent and the solids component and a liquids stream including solvent and the liquids component; and, removing the solids stream from the extractor at a first port and liquids stream from the reactor at a second port. In further embodiments, displacing involves: flowing the solvent through a first end of a reactor having a length of walls segmented into a first length of impermeable walls that are impermeable to the liquids component separated from a second length of impermeable walls that are impermeable to the liquids component by a first length of permeable walls that are permeable to the liquids component, through the first impermeable length of walls toward the permeable length of walls; flowing the fermentation beer into a second end of the reactor through the second length of impermeable walls toward the permeable length of walls, resulting in the solids stream flowing out the extractor at a first port located in the first end of the reactor and the liquids stream flowing out of the reactor through the permeable length of walls. In some embodiments, the methods also involve removing solvent from the solids stream, removing solvent from the liquids stream, or both by converting the solvent to gas.

In some embodiments, the methods of drying beer solids involves exposing a first mixture comprising a liquids portion and a beer solids portion to a solvent under a first set of conditions in which the solvent is in the form of a supercritical fluid or a liquid gas, displacing the liquids portion of the first mixture with the solvent to form a second mixture including the beer solids portion and the solvent; and, removing the solvent from the second mixture. In some embodiments, the first mixture is fermentation beer. In some embodiments, the first mixture is whole stillage. In some embodiments, the first mixture is wet cake. In further embodiments, removing the solvent involves exposing the second mixture to at least a second set of conditions resulting in the solvent converting to a gas, and venting the resultant gas. In yet further embodiments, exposing the second mixture to at least a second set of conditions comprises exposing the second mixture to successively lower pressure conditions, and venting comprises venting any resulting gas after each successive lower pressure condition. In yet further embodiments, the methods also include capturing the vented gas and recompressing the vented gas into a supercritical fluid or liquid gas.

In some embodiments the methods of extracting at least one of oil and ethanol involves exposing a first mixture comprising at least one of oil and ethanol and at least one other component to a solvent in the form of a supercritical fluid or liquid gas under a first set of conditions in which at least one of the oil and ethanol solubilizes in the solvent to form a second mixture; separating the second mixture from the at least one other component; and, removing the solvent from the second mixture. In some embodiments, the first mixture is a slip stream derived from a fermentation reactor. In some embodiments, the first mixture is a fermentation beer. In some embodiments, the first mixture is a fermentation beer after separating out beer solids. In some embodiments, the solvent is supercritical CO2 or liquid CO2 and the first set of conditions is conditions of temperature and pressure in which ethanol but not oil solubilizes in the solvent. In some embodiments, the first set of conditions is conditions of temperature and pressure in which ethanol and oil solubilize in the solvent, and removing the solvent involves: reducing the pressure sufficiently to separate the oil leaving behind a second mixture comprising ethanol and solvent, separating the oil from the second mixture, and thereafter reducing the pressure sufficiently to convert the solvent to gas. In some embodiments, additional purification steps are performed to separate water, which may have been extracted with the ethanol, from the ethanol.

In some embodiments, the systems include a separations reactor configured for use in conjunction with, or configured for integration into, a feedstock-to-ethanol production facility, wherein the separations reactor is suitable for use at conditions supporting a solvent (for example CO2) in a supercritical fluid form, in a liquid gas form, or both; and the separations reactor includes one or more inputs through which a first mixture chosen from a fermentation beer and a mixture derived therefrom is introduced into the separations reactor and through which the solvent is introduced into the separations reactor, and one or more outputs through which separated components of the fermentation beer or mixture derived therefrom are removed from the separations reactor. In some embodiments, the systems further include a solvent in supercritical form or liquid gas form.

In some embodiments, the systems include a feedstock-to-ethanol fermentation production facility; a solvent in supercritical fluid form or liquid gas form; a separations reactor integrated into the fermentation production facility, wherein the separations reactor is suitable for use at conditions supporting the solvent in a supercritical fluid form, in a liquid gas form, or both; and the separations reactor includes one or more inputs through which a first mixture chosen from a fermentation beer and a mixture derived therefrom is introduced into the separations reactor and through which the solvent is introduced into the separations reactor, and one or more outputs through which separated components of the fermentation beer or mixture derived therefrom are removed from the separations reactor.

In some embodiments, the separations reactor (for example of any of the above-referenced systems) has a first impermeable portion joined to a second impermeable portion by a third permeable portion, wherein the first impermeable portion and second impermeable portions are defined by walls that are impermeable to liquids in the first mixture and the third permeable portion is defined by walls that are permeable to liquids in the first mixture; the one or more inputs is a first input located in the first impermeable portion for introducing solvent into the reactor and a second input located in the second impermeable portion for introducing the first mixture into the reactor; and, the one or more outputs is a first output located in the first impermeable section for removing solids in the first mixture from the separations reactor and a second output which is the permeable section. In further embodiments, the separations reactor also comprises a casing with an integral port around the permeable section for capturing the liquids leaving the reactor through the permeable portion and directing them to a next part of the ethanol facility. In further embodiments, the first mixture is fermentation beer, the solids are beer solids and the liquids are beer liquids. In further embodiments, the separations reactor is vertically-oriented with the first impermeable portion being a top end of the reactor and the second impermeable portion being a bottom end of the reactor. In some embodiments, the systems also include an evaporator in fluid communication with the first output, and which evaporator has one or more discharge outlets for releasing gas produced when conditions in the evaporator are set consistent with the solvent converting to a gas phase. In some embodiments, the systems further comprise a compressor in fluid communication with the evaporator for recompressing gas discharged from the evaporator and means for recirculating the recompressed gas back into the separations reactor.

The identified embodiments are exemplary only and are therefore non-limiting. The details of one or more non-limiting embodiments according to the disclosure are set forth in the accompanying drawings and the descriptions below. Other embodiments according to the disclosure should be apparent to those of ordinary skill in the art after consideration of the present disclosure.

DETAILED DESCRIPTION

I. Definitions

Figure 1:
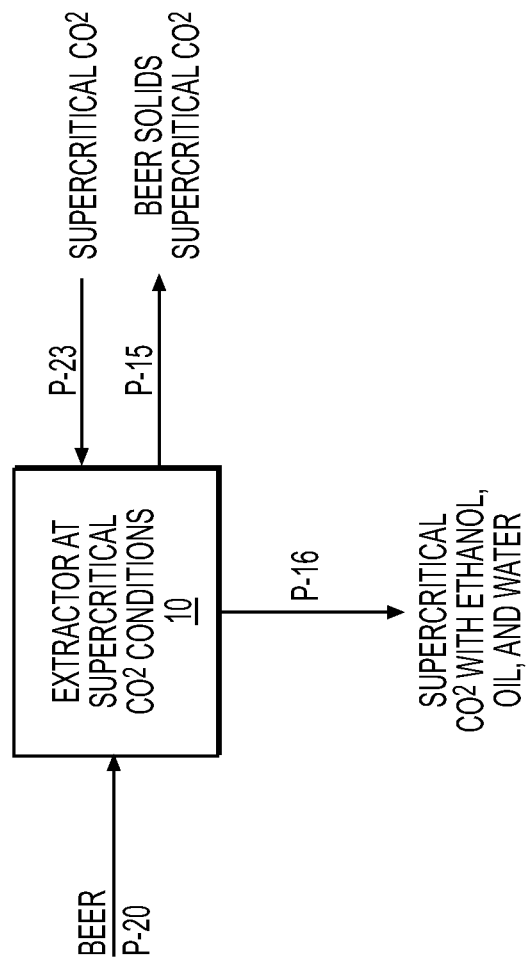
FIG. 1 is a process flow diagram of an embodiment of a method according to this disclosure.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Where ever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error or to permit deviations from the measurements that don't negatively impact the intended purpose. The term "substantially" is meant to permit deviations from the descriptive term that don't negatively impact the intended purpose. All measurements or numbers are implicitly understood to be modified by the word about, even if the measurement or number is not explicitly modified by the word about. All descriptive terms are implicitly understood to be modified by the word substantially, even if the descriptive term is not explicitly modified by the word substantially.

Where ever the terms "a" or "an" are used, "one or more" is understood unless explicitly stated otherwise or such interpretation is nonsensical in context.

Where ever the text refers to displacing/extracting/separating/venting of one component or components from another component or components, it is understood that the action may not result in complete displacement/extraction/separation/venting of the components. For example, where ever the text refers to displacing the liquids fraction from the solids fraction of the wet solids, or extracting the liquids fraction from the solids fraction of the wet solids, or separating the liquids fraction from the solids fraction, it is understood that the phase "at least a portion of" modifies the displaced/extracted/separated fraction regardless of whether or not that phrase explicitly appears in the text, unless specifically stated otherwise. In other words, "displacing the liquids fraction from the solids fraction" means: "displacing at least a portion of the liquids fraction from the solids fraction."

"Liquid gas" refers to a substance that is in the gas phase at room temperature and pressure but may be converted to a liquid phase and used as a solvent in processes according to this disclosure.

The term "purify" and the like does not mean 100% pure but rather only that the target product is not part of the same original mixture in which it is found. Thus, for example, "purifying fermentation products" means that at least a portion of the target product or products is separated from the fermentation mixture, but after separation may include other components from the fermentation mixture as well as the target product.

The present disclosure relates to methods and systems for purifying fermentation products, for example as part of an overall feedstock-to-ethanol fermentation conversion process, such as a corn-to-ethanol fermentation conversion process. Traditionally, the main products of the feedstock-to-ethanol fermentation process are ethanol and beer solids, which can be Dried Distiller's Grain (DDG) in the case of corn-to-ethanol fermentation processes. The products are traditionally derived from the fermentation beer through energy-intensive distillation and drying systems. Fermentation beer can also include oil and water.

In some embodiments, the present disclosure provides approaches to separating out one or more of the products such as ethanol and dried beer solids (e.g. DDG) from the fermentation beer, directly or indirectly, in a more energy efficient manner than the traditional distillation and drying approaches described in the background section. "Directly" means the methods and systems are integrated with fermentation itself, whereas "indirectly" means the methods and systems are applied downstream of fermentation. For example, in some direct embodiments, a novel solvent is used to displace the liquids fraction of the fermentation beer from the solids fraction, resulting in a first mixture of solvent and ethanol (and potentially oil and water) and a second mixture of solvent and beer solids. As another example, in some direct embodiments, a novel solvent contacts a slip stream taken from the fermenter during fermentation. In some indirect embodiments, a novel solvent is used for separation of ethanol or drying of solids after fermentation and distillation.

In some embodiments, the methods and systems for purifying fermentation products relates to the use of a novel solvent as regards ethanol fermentation processes to separate the liquids component of fermentation beer from the solids component of fermentation beer. In some embodiments, the methods and systems for purifying fermentation products relates to the use of the novel solvent to dry the solids component of fermentation beer. The drying methods and systems can be implemented before or after beer distillation.

In some embodiments, the methods and systems for purifying fermentation products relates to the use of the novel solvent to extract oil, extract oil and ethanol, and/or extract ethanol from other process components. The extraction methods and systems can be implemented anywhere during the process flow in which it may be desirable to separate ethanol from other process components, or to separate ethanol and oil together from other process components, or to separate oil from other process components. As a person of skill may understand from reading this specification, water may be extracted along with ethanol. Accordingly, some embodiments involve additional purification steps to separate water and ethanol. Any purification scheme known in the art to separate water and ethanol may be used, such as for example distillation. Alternatively or in addition, water may be separated from ethanol using the novel solvent described herein, in one or more than one iterative separation step.

In general, the methods and systems of this disclosure relate to the use of a novel solvent as regards feedstock-to-ethanol fermentation processes. The novel solvent is a substance in supercritical fluid or liquid gas form, which in some embodiments is used as a "displacent" to displace the liquids component of a mixture from the solids component of a mixture (such as to displace the liquids component of fermentation beer from the solids component of fermentation beer), in some embodiments the novel solvent is used to dry the solids component of fermentation beer, and in other embodiments is used an extraction solvent ("extractant") to remove oil, ethanol, or oil and ethanol from other process components. In some embodiments, the solvent is chosen from substances which under operation conditions (e.g. under conditions in which it is used as a displacent or as an extractant) are in supercritical or liquid gas form.

In some embodiments, the solvent is a supercritical fluid. In some embodiments, the substance which is used in supercritical fluid form is chosen from any substance that has a supercritical phase at temperatures above the freezing temperature of the liquid component and corresponding pressures which result in the supercritical form. In some embodiments, the substance which is used in supercritical form is chosen from any substance that has a supercritical phase at temperatures ranging from greater than 32 degrees F., or greater than 40 degrees F., or greater than 45 degrees F., and corresponding pressures which result In the supercritical form. In some embodiments, the supercritical fluid is chosen such that the amount of energy required to convert it to a gas and thereby dry an amount of wet solids derived from a fermentation beer is favorable (less than) the amount of energy required to drive off water (boil off water) from the same amount of wet solids derived from a fermentation beer. For example, in some embodiments, the solvent can be supercritical $CO_2$ or supercritical nitrogen. In embodiments wherein supercritical $CO_2$ is the solvent, it can be sourced from $CO_2$ produced in the feedstock-to-ethanol conversion process.

In some embodiments, the solvent is a liquid gas. In some embodiments, the solvent is chosen from any liquid gas that has a heat of vaporization less than that of water. In some embodiments, the liquid gas is chosen from any substance that has a liquid phase at temperatures below the critical point and pressures sufficient to hold the gas in liquid phase without solidifying the gas. For example, in some embodiments, the solvent can be a substance that is in liquid gas form at about 10 degrees C. and 50 bar. In some embodiments, the liquid gas is chosen such that the amount of energy required to convert it to a gas and thereby dry an amount of wet solids derived from a fermentation beer is favorable (less than) the amount of energy required to drive off water (boil off water) from the same amount of wet solids derived from a fermentation beer. In some embodiments, the liquid gas is derived from a compound that is in liquid phase at temperatures at or below the boiling point of water at operational pressure, for example below the boiling point of water at atmospheric pressure. For example, in some embodiments, the solvent can be liquid $CO_2$. In embodiments wherein liquid $CO_2$ is the solvent, it can be sourced from $CO_2$ produced in the feedstock-to-ethanol conversion process.

Referring now to the figures, wherein like reference numerals indicate like elements, FIG. 1 is process flow diagram of an embodiment of a method according to this disclosure. As shown, fermentation beer 20 and solvent 23 are brought into contact with one another, for example in a reactor 10 resulting in two product streams: a liquids product stream 16 and a solids product stream 15. The liquids product stream 16 may contain (among other things) ethanol, oil, water and solvent. The solids product stream 15 may contain (among other things) beer solids and solvent. As is understood, separations may be imperfect and consequently the beer liquids stream may include some beer solids, and the beer solids stream may include some liquids such as ethanol.

Figure 2:
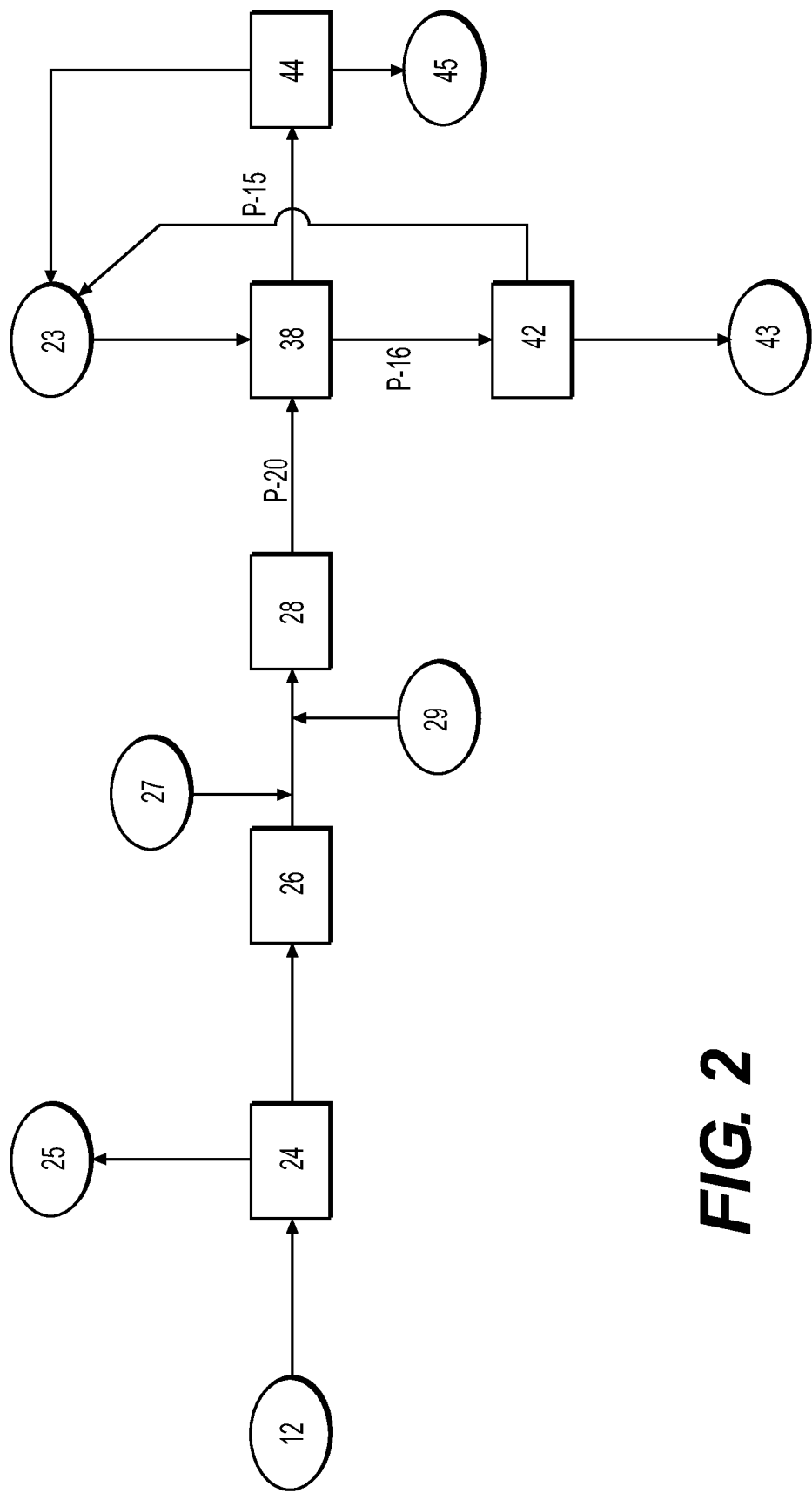
FIG. 2 is process flow diagram of an embodiment of a feedstock-to-ethanol fermentation process in which the method of FIG. 1 may be integrated.

FIG. 2 is a process flow diagram of an embodiment of a feedstock-to-ethanol conversion process in which the method of FIG. 1 may be integrated. As a person of skill understands from reading this disclosure, the conversion process of FIG. 2 is only one conversion process into which methods according to the disclosure may be integrated. Also as a person of skill understands, not all steps shown in FIG. 2 are necessary, and some similar conversion processes may include additional or alternative steps, some of which are identified below.

Turning back to FIG. 2, as shown, feedstock 12 is initially prepared/fractionated 24 for downstream saccharification and fermentation, wherein for example corn kernels are separated into non-fermentable solids 25 (e.g. germ and fiber) and fermentable solids (e.g. endosperm). Once the endosperm has been separated from the non-fermentable solids, it may be ground and directed into a saccharification process 26. Separation and grinding of endosperm may also be conducted in an integrated process. Saccharification process 26 may be a 'cooked' or cold process depending, for example, on the chosen input enzymes, and results in converting starches within the ground endosperm being converted to sugars. A fermentation slurry may be directed from saccharification process 26 to fermentation process 28.

Fermentation process 28 may also receive additional inputs (e.g., yeast 27 and enzymes 29) and may ferment the sugars within the fermentation slurry to produce a certain concentration of ethanol within the fermentation slurry. Fermentation process 28 may produce a certain amount of carbon dioxide ($CO_2$) and other gases, which may be processed through the use of a scrubber or other suitable equipment, and/or be captured and used as a source of solvent such as supercritical $CO_2$ or liquid $CO_2$ in the downstream ethanol separation phase. The main product of fermentation process 28 is beer 20, which comprises a liquids component 16 and a solids component 15. Saccharification process 26 and fermentation process 28 may be performed separately or may be combined into a substantially integrated process.

In some embodiments, the beer 20 is then directed into a separation process 38 such as described in connection with FIG. 1. Here, the beer 20 is contacted with solvent 23 (such as supercritical $CO_2$ or liquid $CO_2$) resulting in two product streams, a liquids product stream 16 and a solids product stream 15. The solids product stream 15 may be directed to an evaporation process 44 (directed to an evaporation system) to remove solvent and produce dried solids 45, whereas the liquids stream 16 may be directed into a separation process 42 (directed to a separation system) to produce ethanol 43. In some embodiments, the separation process 42 may include one or more of: an evaporation process to remove the solvent 23 and a distillation or other process to separate water from ethanol. In some embodiments, the solvent, which has been released from the solids stream 15 and/or the liquids stream 16 may be recycled back into the system, for example for use again in the separation process 38, and/or for example, for use in the separation process 42 to separate water from ethanol. In embodiments, wherein the solvent is released from the solids stream 15 and/or liquids stream 16 in gas phase, it may be directed to a compressor to be recompressed into a supercritical fluid or liquid gas before being recycled back into the system.

Figure 3:
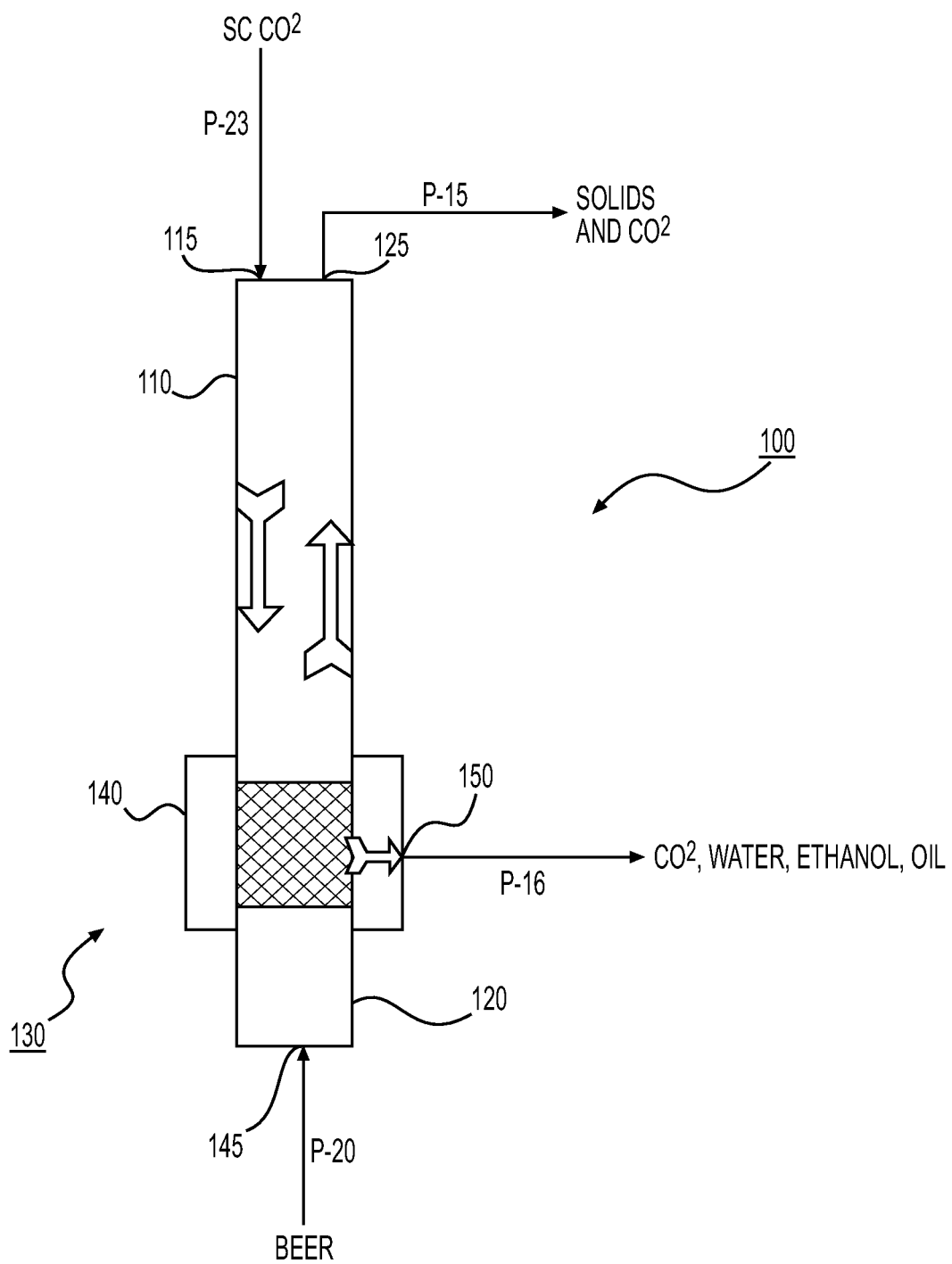
FIG. 3 is a schematic illustration of an embodiment of a separations reactor in which certain methods according to this disclosure may be implemented.

FIG. 3 is a schematic illustration of an embodiment of a reactor 100 in which separation process 38 may be implemented. As shown, the reactor 100 is a conduit comprising an impermeable first portion 110 that is substantially impermeable to fermentation beer liquids separated from an impermeable second portion 120 that is also substantially impermeable to fermentation beer liquids by a permeable portion 130 that is substantially permeable to fermentation beer liquids but not the fermentation beer solids. The permeable portion 130 includes an enclosure 140 which contains fluid flowing out of the permeable portion and directs it through a port 150 to liquid separation system (not shown) such as a distillation system.

The reactor also includes a first port 115 in the first impermeable portion 110, through which solvent enters the reactor 100, a second port 125 also in the first impermeable portion 110 through which a solids product stream containing solvent and beer solids exits the reactor, and a third port 145 at the other end of the reactor in the second impermeable portion 140 through which beer 20 is introduced into the reactor 100. In some embodiments, the reactor 100 is oriented such that solvent flows with the assistance of gravity and beer 20 flows against gravity. For example, the reactor 100 may be oriented substantially vertically, as shown in FIG. 3.

In operation, the reactor 100 is maintained at, or brought to, conditions in which the solvent 23 is in supercritical fluid or liquid gas form. In some embodiments, wherein the solvent 23 is a liquid gas, the reactor conditions are chosen to maintain the substance in liquid form while minimizing the heat of vaporization associated with converting the liquid to gas during the subsequent, evaporation process. Beer 20 is brought into the bottom of the reactor (the second impermeable portion 120 of the reactor in the exemplified embodiment) through port 145 and flows upward. The liquid component 16 of the beer 20 flows out of the reactor at the impermeable portion 130 and is directed to a separations system through port 150. The solids component 15 of the beer 32 continues to flow upward past the permeable portion 130 into the first impermeable portion 110, where it mixes with solvent, which is introduced into the reactor 100 (through the first impermeable portion 110 in the exemplified embodiment) through port 115. In some embodiments, wherein the solvent 23 is a lighter density fluid than the beer 32, the solvent 23 may contribute to pushing the beer liquid 16 out the permeable portion 130. In some embodiments, without wishing to be bound by theory, using a supercritical fluid or liquid gas as a solvent 23 facilitates higher flow rates of solution through the solids 15 with lower pressure because of the reduced viscosity of the supercritical or liquid gas solvent 23 as compared to the beer liquid 16. The solids stream 15, now mixed with solvent 23, leaves the top of the extractor through port 125 and is directed into an evaporation system (not shown).

In some embodiments, the evaporation system may be simply designed to involve decreasing pressure in the system by venting the solids stream to air. In other embodiments, the evaporation system may be designed to reduce pressure as the solids stream passes through just enough to cause the supercritical fluid or liquid gas to change to a gas phase and leave the evaporator. In some embodiments, the now dried solids can leave the evaporator through a gas-tight lock system to be discharged at standard atmospheric conditions.

In some embodiments, the evaporation system may be designed to accommodate a multi-stage evaporation process 44, for example to reduce or minimize the amount of energy needed to recompress the solvent, now in gas phase, back into supercritical or liquid gas form, as compared to the energy required to recompress gas that is formed by reducing conditions to room temperature and pressure. Designing such a process is within the ordinary skill in the art following the principle that the smaller the pressure change between the supercritical form/liquid gas form and gas phase, the less energy is needed to recompress the gas back to supercritical form. By way of example, if the separation operating pressure conditions are 1000 psi, and the supercritical fluid forms a gas at 900 psi, in a first stage of the evaporation process, the pressure may be dropped to 900 psi rather than atmospheric pressure. Despite the conditions being consistent with a change from supercritical fluid form to gas phase, some solvent may remain trapped in the solids. Accordingly, the pressure may then be lowered further to help drive out remaining gas. The number of stages (the number of times the pressure is further reduced) and/or the lowest pressure used for releasing gas is a matter of choice, but may be driven by economic considerations. For example, if the cost of increasing pressure from atmospheric pressure to a final pressure in the evaporator is less than the cost of recovering gas at that final pressure, a person of skill may decide simply to vent gas at that final pressure rather than recover it. In some embodiments, gas released from the system may be brought to a compressor to be recompressed into supercritical fluid or liquid gas and recycled back into the system.

In some embodiments, the (liquid stream) separation system may also utilize the novel solvents according to this disclosure (i.e. supercritical fluid or liquid gas solvents) to target extraction of ethanol, oil, and/or ethanol and oil from other fermentation liquid components, such as water. For example, a supercritical fluid or liquid gas solvent can be chosen in which ethanol preferentially dissolves at certain temperature and pressure conditions relative other fermentation liquid components, or in which ethanol and oil preferentially dissolve at certain temperature and pressure conditions relative other fermentation liquid components. In some embodiments, the solvent is supercritical $CO_2$.

In some embodiments, in operation, as the liquid product stream exiting the separations reactor 100 passes through the (liquid stream) separations system, temperature and pressure conditions are set such that ethanol and oil preferentially solubilize in the solvent as compared to water, resulting in a water phase which can be separated from a product stream comprising ethanol, oil and solvent. The ethanol and oil can then be separated by changing the temperature and pressure conditions (for example by lowering the pressure) such that only ethanol is preferentially solubilized in the solvent. After removing the oil, the conditions of temperature and pressure can again be changed (for example the pressure can be further lowered) so that ethanol may separate from the solvent.

In some embodiments, the separations system involves more than one iteration (i.e. the liquid stream is solubilized in the solvent, the solvent is removed and the product stream is thereafter repeatedly solubilized in the solvent until a target product stream having a desired ethanol content is achieved). In some embodiments, the ethanol may be separated from water using additional or alternative approaches known to those of skill in the art, such as distillation.

The principles described herein wherein a novel solvent is used to dry beer solids and/or to extract ethanol, oil, and or ethanol and oil can be implemented at other points in the fermentation process flow. For example, in the exemplified embodiments, beer solids are dried prior to distillation. However, in an alternative embodiment, the beer solids may be dried using the novel solvent after the fermentation beer is distilled, for example the extraction of dried beer solids can be carried out on whole stillage, or on the wet cake, rather than the beer itself.

As another example of a permutation within scope of this disclosure, the novel solvent can be used to extract oil during fermentation rather than after fermentation (as part of the liquid product stream separation process). For example, a slip steam could be extracted from the fermenter to an extraction tank, which could be a continuous stirred reactor. The solvent could be brought into the tank and mixed with the slip stream. The tank could be brought to or maintained at temperature and pressure conditions wherein the oil is preferentially soluble in the solvent resulting in a mixture of oil and solvent (and ethanol to the extent ethanol has begun to form in the fermenter and is therefore present in the slip stream) as compared to water. The mixture may be transferred to a separator where conditions are changed, for example the pressure is reduced, sufficiently to cause the oil to separate out resulting in a heavy phase containing oil and a light phase containing ethanol and solvent. The light phase can then be passed to another separator where the conditions are changed again (for example the pressure is further lowered) resulting in separation of ethanol from the solvent. Extraction of oil during fermentation could be carried out for a desired time period, including only initially when little ethanol has formed, or until the bulk of the oil is extracted, or throughout fermentation, as some examples.

In another embodiment, the solvent can be used to extract ethanol during fermentation. The process would be similar to the oil extraction process described above, except the slip stream would be exposed to conditions of temperature and pressure in which only ethanol solubilized in the solvent and not also the oil. Processes in which ethanol is removed during fermentation (e.g. which enable the ethanol content to be controlled during fermentation) may facilitate new methods of fermentation in which yeasts or other organisms may be used for sugar conversion, which are not ethanol tolerant. Again, as a person of skill may understand, although ethanol is separated from oil, it may still include some water content. Accordingly, in some embodiments, the ethanol stream may be subjected to additional extractions using the novel solvent, may undergo a distillation process to separate out water, may undergo any other appropriate separation process known to those of skill in the art to separate the water from ethanol, or combinations thereof.

A number of embodiments have been described but a person of skill understands that still other embodiments are encompassed by this disclosure. For example, the use of the solvent to extract ethanol, oil or ethanol and oil, can be implemented anywhere there is a liquid mixture containing ethanol, oil, or ethanol and oil. As another example, extraction techniques using the novel solvents can be combined with other separation techniques. For example, oil could be extracted from beer using the novel solvent and ethanol could be removed using another technology such as mechanical separation. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention.

What is claimed is:

1. A method of purifying feedstock-to-ethanol fermentation products, comprising:
    a. exposing a first mixture chosen from fermentation beer and mixtures derived therefrom to a solvent under a first set of conditions in which the solvent is in a supercritical fluid or liquid gas form thereby generating a second mixture comprising a subset of components of the first mixture and the solvent;
    b. separating the second mixture from remaining components of the first mixture; and,
    c. removing the solvent from the second mixture.

2. A method according to claim 1, wherein the first mixture is chosen from a fermentation beer, whole stillage, and wet cake, and wherein the first mixture comprises a solids portion and a liquids portion, generating comprises displacing the liquids portion from the solids portion with the solvent, and the second mixture comprises the solids portion and the solvent.

3. A method according to claim 2, wherein the first mixture is a pre-distillation fermentation beer.

4. A method according to claim 1, wherein removing comprises exposing the second mixture to a second set of conditions in which the solvent converts to a gas phase.

5. A method according to claim 3, further comprising using a separations reactor to expose the first mixture to the solvent, wherein the separations reactor comprises a length of walls segmented into a first length of impermeable walls connected to a second length of impermeable walls by a length of permeable walls, wherein the first and second length of impermeable walls are impermeable to fermentation liquids and the permeable walls are permeable to fermentation liquids but impermeable to fermentation solids; and, wherein exposing comprises: flowing the solvent into a first end of the separations reactor through the first length of impermeable walls toward the length of permeable walls; flowing the fermentation beer through a second end of the separations reactor through the second length of impermeable walls toward the length of permeable walls, resulting in a fermentation solids stream exiting the separations reactor at a first port in the in the first end of the separations reactor and the fermentation liquids exiting the separations reactor through the permeable length of walls.

6. A method according to claim 1, wherein the first set of conditions are chosen to result in at least one of ethanol and oil solubilizing in the solvent generating a second mixture comprising ethanol, oil or both, according to the first set of conditions, and solvent.

7. A method according to claim 1, wherein the fermentation beer comprises a liquids portion and a solids portion and the first mixture comprises the liquids portion of the fermentation beer, and further wherein the first set of conditions are chosen to result in ethanol and oil present in the liquids portion solubilizing in the solvent, and removing comprises:
    a. exposing the second mixture to a second set of conditions in which oil separates out of the second mixture resulting in a third mixture comprising ethanol and solvent;
    b. separating the oil from the third mixture;
    c. exposing the third mixture to a third set of conditions in which ethanol separates out of the solvent;
    d. exposing the solvent to a fourth set of conditions in which the solvent converts to gas; and,
    e. venting the gas.

8. A method according to claim 7, wherein the vented gas is captured and directed to a compressor to be recompressed into supercritical fluid or liquid gas.

9. A method according to claim 7, further comprising separating water from ethanol.

10. A method according to claim 1, wherein the first mixture is a slip stream from a fermenter, and the first set of conditions is chosen to solubilize oil in the solvent to generate the second mixture.

11. A system, comprising:
    a. an ethanol production facility for producing ethanol from a feedstock using a fermentation process;
    b. a solvent in supercritical fluid or liquid gas form; and,
    c. a separations reactor integrated into the ethanol production facility, wherein the separations reactor is suitable for use at conditions supporting the solvent in a supercritical fluid or liquid gas form, or both; the separations reactor comprising:
        i. one or more inputs for receiving the solvent and a first mixture chosen from a fermentation beer and mixtures derived therefrom; and,
        ii. one or more outputs for removing a second mixture comprising the solvent and a subset of components of the first mixture and for removing remaining components of the first mixture.

12. A system according to claim 11, wherein: the separations reactor comprises a first impermeable portion joined to a second impermeable portion by a third permeable portion, wherein the first impermeable portion and second impermeable portion are defined by walls that are impermeable to fermentation liquids and the permeable portion is defined by walls that are permeable to fermentation liquids and impermeable to fermentation solids; the one or more inputs is a first input located in the first impermeable portion for introducing solvent into the separations reactor and a second input located in the second impermeable portion for introducing fermentation beer into the separations reactor; and the one or more outputs is a first output located in the first impermeable portion for removing a mixture comprising fermentation solids and solvent from the reactor and a second output which is the permeable walls for removing a mixture comprising fermentation liquids and solvent from the reactor.

13. A system according to claim 12, wherein the separations reactor further comprises and enclosure with an integral port surrounding the permeable portion to capture the mixture exiting the separations reactor at the permeable portion and direct the mixture to a next part of the system.

14. A system according to claim 12, wherein the separations reactor has a top portion which is the first impermeable portion and a bottom portion which is the second impermeable portion and the separations reactor is vertically-oriented such that solvent may flow assisted by gravity and fermentation beer may flow against gravity.

15. A system according to claim 13, further comprising an evaporator in fluid communication with the first output, and which evaporator has one or more discharge outlets for releasing gas produced when conditions in the evaporator are set consistent with the solvent converting to a gas phase.

16. A system according to claim 15, wherein the system further comprises: a compressor in fluid communication with the evaporator for recompressing gas discharged from the evaporator; and, means for recycling the recompressed gas back into the solids extractor.

* * * * *